United States Patent [19]

Hartman

[11] 4,438,266
[45] Mar. 20, 1984

[54] TRIAZOLOPYRAZINAMINES USEFUL AS ADJUNCTS TO RADIATION THERAPY

[75] Inventor: George D. Hartman, Lansdale, Pa.

[73] Assignee: Merck & Co., Inc., Rahway, N.J.

[21] Appl. No.: 379,232

[22] Filed: May 17, 1982

[51] Int. Cl.$^3$ ............... C07D 487/04; A61K 31/495; C07D 241/20
[52] U.S. Cl. .................................... 544/350; 544/409; 424/250
[58] Field of Search .................. 544/350; 424/250

[56] References Cited

U.S. PATENT DOCUMENTS

| | | | |
|---|---|---|---|
| 3,541,093 | 11/1970 | Tull et al. | 544/350 |
| 3,629,260 | 12/1971 | Maquire et al. | 544/350 |
| 3,660,397 | 5/1972 | Jones et al. | 544/350 |
| 3,976,644 | 8/1976 | McGregor et al. | 544/409 |

FOREIGN PATENT DOCUMENTS 1232758 5/1971 United Kingdom .

OTHER PUBLICATIONS

Cragoe et al., *J. Med. Chem.*, 10 66, (1967).

Primary Examiner—Mark L. Berch
Assistant Examiner—Chabi Kalita
Attorney, Agent, or Firm—Thomas E. Arther; David L. Rose; Mario A. Monaco

[57] ABSTRACT

8-Halo-6-nitro-1,2,4-triazolo[4,3-a]pyrazine and its corresponding 3-alkyl derivatives are prepared by converting amino-5,6-dichloropyrazinecarboxylic acid to 5-chloro-6-hydrazino-3-nitropyrazinamine and treating said hydrazino compound with a lower alkyl ortho ester of a loweraliphatic carboxylic acid to produce an 8-chloro-6-nitro-1,2,4-triazolo[4,3-a]pyrazine-5-amine or the corresponding 3-loweralkyl derivatives thereof.

3 Claims, No Drawings

TRIAZOLOPYRAZINAMINES USEFUL AS ADJUNCTS TO RADIATION THERAPY

BACKGROUND OF THE INVENTION

This invention relates to 8-halo-6-nitro-1,2,4-triazolo[4,3-a]pyrazine 5-amine compounds and the acid addition salts thereof, used to selectively sensitize tumor cells to therapeutic radiation and thus increase the effective therapeutic ratio of radiologic treatment. In addition, the present invention relates to pharmaceutical compositions comprising such pyrazine compounds and to methods of treatment comprising administering such compounds to patients undergoing radiation therapy to enhance the effectiveness of such treatment.

At the present time, certain other unrelated compounds are in experimental clinical use as radiation sensitizers. However, these compounds—for example, metronidazole and misonidazole—suffer from the drawback that they also cause symptoms of neurotoxicity which limits their usefulness. The compounds of the present invention are effective radiation sensitizers, but are believed to have a more favorable therapeutic ratio.

DETAILED DESCRIPTION OF THE INVENTION

The compounds of the present invention which are useful as radiation sensitizers are novel 3-substituted derivatives of 8-chloro-6-nitro-1,2,4-triazolo[4,3-a]pyrazinamines and the acid addition salts thereof of the formula:

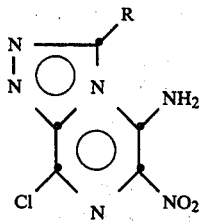

wherein R is hydrogen or methyl. The corresponding acid addition salts are formed by reaction of the above amino compound with an equimolar amount of a strong mineral acid such as hydrochloric acid, hydrobromic acid, sulfuric and phosphoric acids.

The triazolopyrazinamines described above are prepared from the known 3-amino-5,6-dichloropyrazine carboxylic acid E. J. Cragoe, Jr., O. W. Woltersdorf, Jr., J. B. Bicking, S. F. Kwong, J. H. Jones, *J. Med. Chem.*, 10, 66 (1967). The carboxylic acid is dissolved in sulfuric acid or fuming sulfuric acid. To the solution formed in this manner, a mixture of equal volumes of sulfuric and nitric acid or the corresponding fuming sulfuric and fuming nitric acids are added to the solution to effect replacement of the carboxylic acid substituent by a nitro-substituent as disclosed in detail in Case 16550IA, U.S. Ser. No. 295,446, now abandoned Example IA filed Aug. 24, 1981 with production of 5,6-dichloro-3-nitropyrazinamine, the starting material used in the present process.

In accordance with the present invention, the starting material, 5,6-dichloro-3-nitropyrazinamine I is contacted with an equimolar amount of hydrazine to produce as an intermediate 5-chloro-6-hydrazino-3-nitropyrazinamine II and said hydrazinopyrazinamine is then contacted with a loweralkyl ortho ester of a lower aliphatic carboxylic acid of the formula

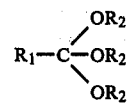

wherein $R_1$ is methyl or ethyl and $R_2$ is a lower aliphatic radical, to produce an 8-chloro-6-nitro-1,2,4-triazolo[4,3-a]pyrazine-5-amine III or the 3-methyl derivative thereof as disclosed in the flow sheet which follows:

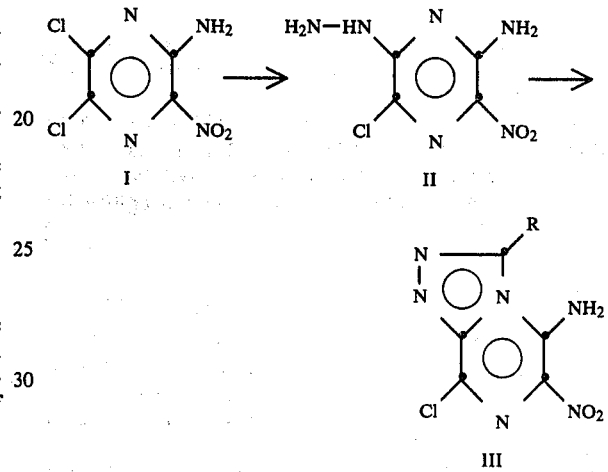

wherein R is selected from hydrogen or methyl.

In carrying out the first step of applicants' novel process, the reaction of the dichloronitropyrazine I with the hydrazine reagent is preferably carried out in a solvent for the reactant. The solvent employed is a lower alkanol such as methanol, ethanol, isopropanol; ethers such as tetrahydrofuran; dimethyl formamide; and acetonitrile. The hydrazine reactant is preferably present in approximately a 100% molar excess over the nitropyrazine. In carrying out the reaction a solution of the hydrazine is prepared and the dichloronitropyrazinamine is added in portions, thus keeping an excess of hydrazine reagent always present. The hydrazine intermediate II separates as a solid and is recovered by filtration. The hydrazine intermediate II is recovered as a crude solid which is used directly in the next reaction step. It may be characterized by reaction with acetone to form the corresponding isopropylidene derivative.

The final product III is prepared by heating at a temperature of 50°–120° C. for 1–3 hours the hydrazine intermediate II with a loweralkyl ortho ester of a lower aliphatic carboxylic acid, i.e., trimethyl or ethyl orthoformate or trimethyl or ethyl orthoacetate to produce in the case of the formate ester the product 8-chloro-6-nitro-1,2,4-triazolo[4,3-a]pyrazine-5-amine IIIA and in the case of the acetate ester 8-chloro-3-methyl-6-nitro-1,2,4-triazolo[4,3-a]pyrazine-5-amine, IIIB.

As indicated hereinabove acid addition salts of compounds of Formula I may be prepared by mixing a selected compound of Formula I with an equimolar amount of a strong mineral acid in a solvent for the reactants at a temperature of 0° to 50° C.

The method of treatment of human patients or domestic animals undergoing radiation treatment of malignant disease processes employs the compounds of the present invention in pharmaceutical compositions that are administered orally or parenterally, preferably intravenously. The dose employed depends on the radiation protocol for each individual patient. In protocols where the radiation dose is divided into a large number of fractions, the drug can be administered at intervals in the schedule and not necessarily with each radiation treatment. In general, the drug is administered from 10 minutes to 5 hours prior to the radiation treatment in a dosage amount of between 0.25 to about 4.0 grams per square meter of body surface.

Oral dosage forms such as tablets, capsules, or elixirs may be employed.

Capsules containing from 100 to 500 mg. of drug/capsule are preferred for use in the method of treatment of our invention.

The following examples are intended to illustrate but do not limit the process of preparation, product, compositions, or method of treatment aspects of the invention. Temperatures are expressed in degrees Celsius throughout the examples.

EXAMPLE 1

5-Chloro-6-hydrazino-3-nitropyrazineamine

To 300 ml of ethanol was added 7.4 g (0.22 mole) of a 95% hydrazine solution. This solution was cooled to 10° and with stirring 20.9 g (0.1 mole) of 5,6-dichloro-3-nitropyrazinamine (1) was added portionwise. A dark precipitate formed immediately and the suspension was stirred for 1 hour at room temperature. The mixture was filtered and the resulting solid washed with ethanol, water, ethyl acetate, ethanol and air dried to afford 18.0 g (88%) of the desired hydrazine as a brown solid, m.p. 220°; ms:m/e 205. This solid was treated with acetone to form the isopropylidene derivative, m.p. 245°–246° (dec.).

Anal. Calcd. for $C_7H_9ClN_6O_2$: C, 34.37; H, 3.71; N, 34.35; Found: C, 33.32; H, 3.60; N, 33.20.

EXAMPLE 2

8-Chloro-6-nitro-1,2,4-triazolo[4,3-a]pyrazine-5-amine

To 5.0 g (0.024 mole) 5-chloro-6-hydrazino-3-nitropyrazinamine was added 50 ml of triethylorthoformate and the resulting suspension was heated at 100° for 1 hour. The reaction mixture was cooled, filtered and the dark brown solid washed with chloroform to give 3.9 g (77%) of 8-chloro-6-nitro-1,2,4-triazolo[4,3-a]pyrazine-5-amine as a brown solid, m.p. 220°, H' nmr (DMSO-$d^6$): 9.65 (2H, broad singlet), 9.95 (1H, singlet); ms:m/e 214.

EXAMPLE 3

8-Chloro-3-methyl-6-nitro-1,2,4-triazolo[4,3-a]pyrazine-5-amine

To 5.0 g (0.024 m) 5-chloro-6-hydrazino-3-nitropyrazinamine was added 50 ml of triethylorthoacetate and the resulting suspension was heated at 100° for 2.5 hours. The reaction mixture was cooled, filtered and the resulting dark brown solid washed with chloroform to give 4.1 g (75%) of the titled product as a brown solid, m.p. 220°; H' nmr (DMSO-$d^6$): 9.60 (2H, broad singlet), 3.40 (3H, s); ms:m/e 228.

EXAMPLE 4

Capsules

Suitable formulations for oral administration are prepared by filling appropriately sized capsules individually with 100 and 500 mg portions of each of the compounds produced in accordance with Examples 2 and 3 inclusive.

What is claimed is:

1. A compound of the formula:

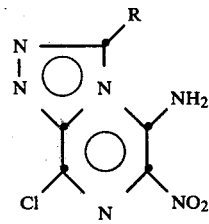

wherein R is hydrogen or methyl and pharmaceutically acceptable acid addition salts thereof.

2. A compound according to claim 1 which is 8-chloro-6-nitro-1,2,4-triazolo[4,3-a]pyrazine-5-amine.

3. A compound according to claim 1 which is 8-chloro-3-methyl-6-nitro-1,2,4-triazolo[4,3-a]pyrazine-5-amine.

* * * * *